United States Patent  (10) Patent No.: US 9,799,499 B2
Kobayashi et al.  (45) Date of Patent: Oct. 24, 2017

(54) MASS SPECTROMETRIC METHOD, MASS SPECTROMETER, AND MASS SPECTROMETRIC DATA PROCESSING PROGRAM

(71) Applicant: SHIMADZU CORPORATION, Kyoto (JP)

(72) Inventors: Yuko Kobayashi, Kusatsu (JP); Tairo Ogura, Columbia, MD (US)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/039,924

(22) PCT Filed: Nov. 28, 2013

(86) PCT No.: PCT/JP2013/082007
§ 371 (c)(1),
(2) Date: Jun. 21, 2016

(87) PCT Pub. No.: WO2015/079529
PCT Pub. Date: Jun. 4, 2015

(65) Prior Publication Data
US 2017/0032947 A1  Feb. 2, 2017

(51) Int. Cl.
H01J 49/26  (2006.01)
H01J 49/00  (2006.01)
(Continued)

(52) U.S. Cl.
CPC ........ H01J 49/005 (2013.01); G01N 30/7266 (2013.01); H01J 49/0036 (2013.01); H01J 49/4215 (2013.01)

(58) Field of Classification Search
CPC ...... H01J 49/005; H01J 49/4215; H01J 49/26; H01J 49/0027
(Continued)

(56) References Cited

U.S. PATENT DOCUMENTS

2007/0262253 A1* 11/2007 Guo .................. G01N 33/6848
250/283
2008/0021687 A1  1/2008 Hunter et al.
(Continued)

FOREIGN PATENT DOCUMENTS

JP  2012002544 A  1/2012
JP  2012-104389 A  5/2012
JP  2013-15485 A  1/2013

OTHER PUBLICATIONS

International Search Report for PCT/JP2013/082007 dated Jan. 7, 2014.
(Continued)

Primary Examiner — Nicole Ippolito
(74) Attorney, Agent, or Firm — Sughrue Mion, PLLC

(57) ABSTRACT

In a mass spectrometric method of the invention, a mass spectrometer (2) is used having a mass separation unit (231, 234) before and after a collision cell (232) for fragmenting ions. When a product ion corresponding to a precursor ion set for a sample is selected by performing product ion scan with respect to the precursor ion, an exclusion range of mass-to-charge ratios is set based on information on non-selection ions input by a user, and a product ion that satisfies a predefined criterion is selected within a range of mass-to-charge ratios excluding the exclusion range in a product ion spectrum. According to the mass spectrometric method of the invention, product ions suited for measurement on a target compound can be selected.

8 Claims, 3 Drawing Sheets

(51) Int. Cl.
*G01N 30/72* (2006.01)
*H01J 49/42* (2006.01)

(58) Field of Classification Search
USPC .................................... 250/281, 282, 283
See application file for complete search history.

(56) References Cited

U.S. PATENT DOCUMENTS

| | | | |
|---|---|---|---|
| 2009/0294648 A1* | 12/2009 | Schneider | H01J 49/004 250/282 |
| 2012/0138788 A1* | 6/2012 | Taniguchi | H01J 49/004 250/287 |
| 2014/0224973 A1* | 8/2014 | Sekiya | H01J 49/0481 250/282 |
| 2016/0268112 A1* | 9/2016 | Yip | H01J 49/0031 |

OTHER PUBLICATIONS

Written Opinion for PCT/JP2013/082007 dated Jan. 7, 2014.
Communication dated Nov. 15, 2016, issued by the Japan Patent Office in corresponding Japanese Application No. 2015-550263.

* cited by examiner

MASS SPECTROMETRIC METHOD, MASS SPECTROMETER, AND MASS SPECTROMETRIC DATA PROCESSING PROGRAM

CROSS REFERENCE TO RELATED APPLICATIONS

This application is a National Stage of International Application No. PCT/JP2013/082007 filed Nov. 28, 2013, the contents of which are incorporated herein by reference in their entirety.

TECHNICAL FIELD

The present invention relates to a mass spectrometric method, a mass spectrometer, and a mass spectrometric data processing program for selecting a pair of a precursor ion and a product ion that is used to perform qualitative determination and/or quantitative determination of a target compound contained in a sample through multiple reaction monitoring (MRM) measurement.

BACKGROUND ART

A technique called MS/NTS analysis (tandem mass spectrometry) has been widely used as one of techniques for mass spectrometry, in order to perform identification, structural analysis, or quantitative determination of a high molecular-weight substance. Various configurations have been proposed for mass spectrometers for the MS/MS analysis, and a tandem quadrupole mass spectrometer is normally used because of the simple structure and easy operation and handling.

In the tandem quadrupole mass spectrometer, ions generated from an ion source and originating from a compound are introduced into a front-stage quadrupole mass filter (usually represented as Q1), and ions each having a specific mass-to-charge ratio m/z are sorted out as precursor ions. The precursor ions are introduced into a collision cell in which a quadrupole (or higher multipole) ion guide (usually represented as q2) is housed. Collision-induced dissociation (CID) gas such as argon is supplied into the collision cell, and the precursor ions collide with the CID gas in the collision cell, so that precursor ions are fragmented and various product ions are generated. The product ions are introduced into a rear-stage quadrupole mass filter (usually represented as Q3), and product ions each having a specific mass-to-charge ratio m/z are sorted out and reach a detector to be detected.

An MRM measurement mode is one of MS/MS measurement modes in the tandem quadrupole mass spectrometer. In the MRM measurement mode, fixed mass-to-charge ratios are used for ions that can pass through the front-stage quadrupole mass filter and the rear-stage quadrupole mass filter, and the intensity (amount) of specific product ions corresponding to specific precursor ions is measured. In such MRM measurement, ions originating from non-targeted compounds and foreign components and neutral particles can be removed by the two-stage mass filters, and hence an ion intensity signal having a high SN ratio can be obtained. Accordingly, the MRM measurement is particularly effective for quantitative determination of a slight amount of component and the like.

Such a tandem quadrupole mass spectrometer as described above is used alone in some cases, and is used in combination with a liquid chromatograph (LC) or a gas chromatograph (GC) in many cases. For example, an LC/MS/MS including a tandem quadrupole mass spectrometer as a detector of a liquid chromatograph is frequently used, for example, for quantitative analysis on compounds included in a sample containing a large number of compounds and a sample including foreign substances.

In the case of performing an MRM measurement by the LC/MS/MS (or GC/MS/MS), prior to measurement on a target sample, the combination (hereinafter, referred to as the "MRM transition") of the mass-to-charge ratio of target precursor ions and the mass-to-charge ratio of target product ions needs to be set as one of measurement conditions, in association with the retention time of each target compound. By setting the MRM transition best suited for each target compound, the signal intensity of ions originating from each target compound can be obtained with high accuracy and sensitivity, and quantitative determination of the target compound can be performed with high accuracy and sensitivity. Although the MRM transition can be manually set by an analysis operator, the manual setting is troublesome, and the best combination cannot necessarily be set.

In view of the above, the MRM transition is conventionally set in the following manner.

First, an analysis operator specifies only the mass-to-charge ratios of precursor ions originating from a target compound. Consequently, product ion scan measurement concerning the specified precursor ions is performed on a known sample containing the target compound, and a predetermined number of product ion peaks are selected in the order of higher signal intensity on a product ion spectrum obtained as a result of the product ion scan measurement. Then, the combination of the precursor ions specified by the analysis operator and product ions corresponding to the selected peaks is defined as the MRM transition.

According to the above-mentioned method, even if the analysis operator does not know the mass-to-charge ratio of target product ions, appropriate product ions are found, and the MRM transition can be automatically set. However, the kind of generated product ions may be different depending on parameters such as the magnitude of collision energy (CE) voltage applied to fragment precursor ions, and product ions generated only under a certain restricted condition may exhibit high signal intensity. Hence, product ions exhibiting low signal intensity may be more suited for quantitative determination than product ions exhibiting high signal intensity. To deal with this, for example, in a proposed method, product ion scan measurement is performed several times, and product ions are selected in the order of larger appearance frequency on each of product ion spectra obtained as a result of the product ion scan measurement (for example, Patent Literatures 1 and 2).

CITATION LIST

Patent Literature

[Patent Literature 1] JP 2013-15485 A
[Patent Literature 2] JP 2012-104389 A

SUMMARY OF INVENTION

Technical Problem

According to conventional methods, a predetermined number of product ion peaks are selected in the order of higher signal intensity or in the order of larger appearance frequency on a product ion spectrum obtained by performing product ion scan. In these methods, the mass-to-charge ratio of selected product ions is not considered, and the selected product ions may not necessarily be ions that characterize the structure of a target compound. If such product ions are set to the MRM transition, there arises a problem of confusion and a compound different from the target compound may be detected, leading to an incorrect result in qualitative determination or an error in quantitative determination.

One of ions that are inappropriate to be selected as product ions is a precursor on that is not fragmented (that is, a precursor ion itself). In the case where a precursor ion is a monovalent ion and is detected as a product ion without being fragmented the mass-to-charge ratios of the precursor ion and the product ion are the same as each other, and hence an analysis operator can recognize that the detected precursor ion is inappropriate as the product ion, and can set the MRM transition again. Moreover, in the case where a precursor ion is a monovalent ion, by setting the range of mass-to-charge ratios smaller than the mass-to-charge ratio of the precursor ion as a product ion measurement range, selection of a precursor ion itself can be avoided.

However, when a multivalent precursor ion is fragmented, some of product ions have a reduced valence, and may have a mass-to-charge ratio higher than the mass-to-charge ratio of the precursor ion, in which case the range of the mass-to-charge ratios of product ions must not be limited as described above. Moreover, the mass-to-charge ratio of the precursor ion changes when its valence changes. A problem in this case is that the analysis operator may not recognize that the ion is substantially the same as the precursor ion, and sets the MRM transition in which the ion is set as a product ion, leading to an incorrect result in qualitative determination or an error in quantitative determination.

An object of the present invention is to provide a mass spectrometric method, a mass spectrometer, and a mass spectrometric program capable of selecting product ions suited for qualitative determination and quantitative determination of a target compound, at the time of determining an MRM transition as a parameter for MRM measurement.

Solution to Problem

A first form of the present invention, which has been made in order to achieve the above-mentioned object, is a mass spectrometric method, using a mass spectrometer having a mass separation unit before and after a collision cell for fragmenting ions, for selecting a product ion corresponding to a precursor ion set for a sample by performing product ion scan with respect to the precursor ion, the method including:

a) setting one or a plurality of mass-to-charge ratios based on information on non-selection ions input by a user; and b) selecting a product ion that satisfies a predefined criterion within a range excluding the one or a plurality of mass-to-charge ratios in a product ion spectrum obtained by the product ion scan.

The information input by a user is typically a numerical value of the mass-to-charge ratio, and any other information such as an ionic formula for non-selection ion may be used as long as the mass-to-charge ratio can uniquely be determined from the information.

The above-mentioned criterion may include selecting a product ion that has the largest mass peak intensity, selecting a product ion that has the largest mass peak appearance frequency, etc.

In the method according to the first form of the present invention, product ions are selected after excluding undesired ions, which are product ions generated from a target compound but are not characteristic ions with respect to the target compound. Accordingly, product ions suited for measurement on the target compound can be selected. The above-mentioned undesired ions include, for example, ions identical to the precursor ion, ions in which only the valence of the precursor ion changes, isotope ions, and dehydrated ions of the precursor ion.

When qualitative determination is performed on the target compound in MRM measurement, two kinds of MRM transitions are used and the ratio of detected intensities for the MRM transitions is verified to confirm the target compound. Depending on the kind of foreign components included in the sample, the mass-to-charge ratio of product ion set as the MRM transition for the target compound may have a similar value to that of product ion generated from the foreign components, in which case the MRM transition may be inappropriate.

Accordingly, in the method according to the first form, it is preferable to select a user-specified number of product ions that satisfy the above-mentioned predefined criterion.

A second form of the present invention, which has been made in order to achieve the above-mentioned object, provides a mass spectrometer having a mass separation unit before and after a collision cell for fragmenting ions, the mass spectrometer being for selecting a product ion corresponding to a precursor ion set for a sample by performing product ion scan with respect to the precursor ion, the mass spectrometer including:

a) a non-selection ion setting unit for setting one or a plurality of mass-to-charge ratios based on information on non-selection ions input by a user; and b) a product ion selection unit for selecting a product ion that satisfies a predefined criterion within a range excluding the one or a plurality of mass-to-charge ratios in a product ion spectrum obtained by the product ion scan.

A third form of the present invention, which has been made in order to achieve the above-mentioned object, is a mass spectrometric data processing program, using a mass spectrometer having a mass separation unit before and after a collision cell for fragmenting ions, for selecting a product ion corresponding to a precursor ion from a product ion spectrum obtained set for a sample by performing product ion scan with respect to the precursor ion, the mass spectrometric data processing program causing a computer capable of accessing a storage unit in which the product ion spectrum is stored to function as:

a) a non-selection ion setting unit for setting one or a plurality of mass-to-charge ratios based on information on non-selection ions input by a user; and b) a product ion selection unit for selecting a product ion that satisfies a predefined criterion within a range excluding the one or a plurality of mass-to-charge ratios in a product ion spectrum obtained by the product ion scan.

Advantageous Effects of Invention

In the mass spectrometric method, the mass spectrometer, and the mass spectrometric data processing program according to the present invention, product ions are selected after excluding undesired ions, which are also product ions generated from a target compound but do not characterize the target compound. Accordingly, product ions suited for measurement on the target compound can be selected.

DESCRIPTION OF EMBODIMENTS

Figure 1:
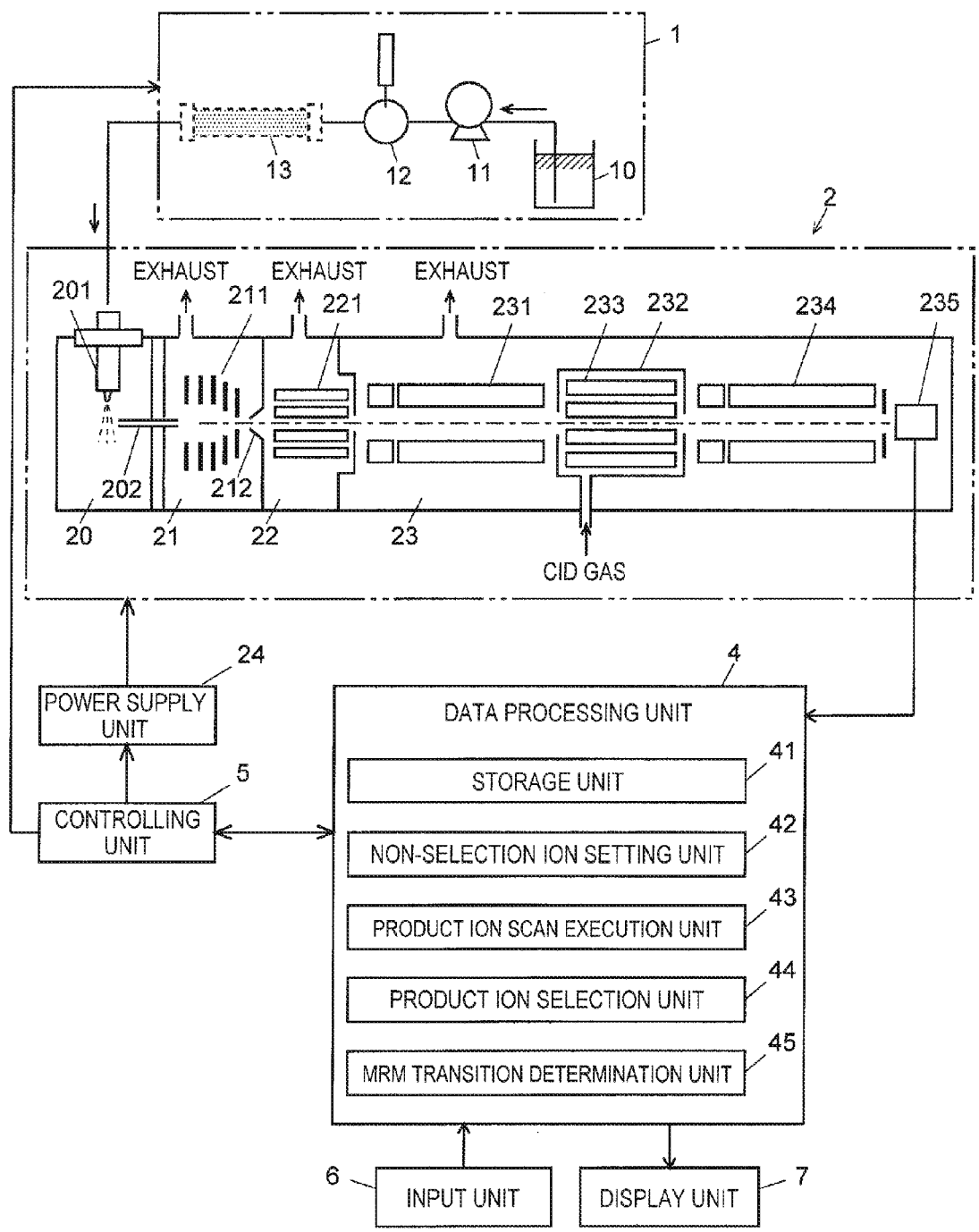
FIG. 1 is a main part configuration diagram of a liquid chromatograph mass spectrometer as one embodiment of a mass spectrometer according to the present invention.

Hereinafter, an embodiment of a liquid chromatograph mass spectrometer including a tandem quadrupole mass spectrometer according to the present invention is described with reference to the drawings. FIG. 1 is a main part configuration diagram of a liquid chromatograph mass spectrometer of the present embodiment.

In the liquid chromatograph mass spectrometer of the present embodiment, a liquid chromatograph unit 1 includes: a mobile-phase container 10 for holding a mobile phase; a pump 11 for drawing the mobile phase and sending the mobile phase at a fixed flow rate; and an injector 12 for injecting a previously prepared sample at a predetermined amount into the mobile phase. In the present embodiment, a preparation of a target compound is subjected to flow injection analysis, a MRM method used to analyze the target compound is created, and hence a column is not used. At the time of analyzing an actual sample, a column 13 (broken lines) for temporally separating various compounds included in the sample is used. The pump 11 draws the mobile phase from the mobile-phase container 10 and sends the mobile phase at the fixed flow rate. A sample solution of the preparation is introduced at a predetermined amount from the injector 12 into the mobile phase, and is introduced to a mass spectrometer 2 while being carried by the mobile phase flow.

The mass spectrometer 2 has a configuration of a multiple-stage differential pumping system including: an ionization chamber 20 set to a substantially atmospheric pressure; a high-vacuum analysis chamber 23 that is exhausted to vacuum by a vacuum pump (not illustrated); and first and second intermediate vacuum chambers 21 and 22 whose degrees of vacuum are increased in stages, and which are arranged between the ionization chamber 20 and the high-vacuum analysis chamber 23. The ionization chamber 20 is provided with an electrospray ionization probe (ESI probe) 201 for spraying the sample solution while applying an electric charge to the sample solution, and the ionization chamber 20 and the rear-stage first intermediate vacuum chamber 21 are communicated with each other by a small-diameter heating capillary 202. The first intermediate vacuum chamber 21 and the second intermediate vacuum chamber 22 are partitioned by a skimmer 212 including a small hole in its apex part, and the first intermediate vacuum chamber 21 and the second intermediate vacuum chamber 22 are respectively provided with ion guides 211 and 221 for transporting ions to the rear stage while focusing the ions. The analysis chamber 23 is provided with: a collision cell 232 in which a multipole ion guide (q2) 233 is provided; a front-stage quadrupole mass filter (Q1) 231 for separating ions in accordance with their mass-to-charge ratios; a rear-stage quadrupole mass filter (Q3) 234 for similarly separating ions in accordance with their mass-to-charge ratios; and an ion detector 235, and the collision cell 232 is arranged between the front-stage quadrupole mass filter (Q1) 231 and the rear-stage quadrupole mass filter (Q3) 234.

At the time of MS/MS analysis, CID gas such as argon or nitrogen is continuously or intermittently supplied into the collision cell 232. A power supply unit 24 applies a predetermined voltage to each of the electrospray ionization probe 201; the ion guides 211, 221, and 233, and the quadrupole mass filters 231 and 234. Each of the quadrupole mass filters 231 and 234 includes a pre-rod electrode in the front stage of a main rod electrode, for correcting disturbance of an electric field at its entrance terminal, and a voltage different from that applied to the main rod electrode can be applied to the pre-rod electrode.

In the mass spectrometer 2, when eluate from the column 13 reaches the ESI probe 201, the eluate is sprayed from the tip of the probe 201 while an electric charge is applied to the eluate. Charged droplets formed by the spraying are fragmented into finer particles by an action of electrostatic force due to the applied electric charge. In this process, the solvent evaporates so that ions originating from a compound are generated. The ions are sent to the first intermediate vacuum chamber 21 through the heating capillary 202, are focused by the ion guide 211, and are sent to the second intermediate vacuum chamber 22 through the small hole in the apex part of the skimmer 212. Then, the ions originating from the compound are focused by the ion guide 221, are sent to the analysis chamber 23, and are introduced into the space in the long-axis direction of the front-stage quadrupole mass filter 231. The ionization method is not limited to the electrospray ionization method, and an atmospheric pressure chemical ionization method, an atmospheric pressure photoionization method, and other ionization methods may be adopted.

At the time of performing MS/MS analysis by the mass spectrometer 2, a predetermined voltage (a voltage obtained by superimposing a high-frequency voltage and a direct-current voltage) is applied from the power supply unit 24 to each of the rod electrodes of the front-stage quadrupole mass filter 231 and the rear-stage quadrupole mass filter 234, and CID gas is continuously or intermittently supplied into the collision cell 232. Among various ions sent into the front-stage quadrupole mass filter 231, only ions having a specific mass-to-charge ratio corresponding to the voltage applied to each rod electrode of the front-stage quadrupole mass filter 231 pass through the filter 231 and are introduced as precursor ions to the collision cell 232. In the collision cell 232, the precursor ions collide with the CID gas and dissociate, so that various product ions are generated. When the generated various product ions are introduced to the rear-stage quadrupole mass filter 234, only product ions having a specific mass-to-charge ratio corresponding to the voltage applied to each rod electrode of the rear-stage quadrupole mass filter 234 pass through the filter 234 and reach the ion detector 235 to be detected by the ion detector 235. The ion detector 235 is, for example, a pulse-count detector, and outputs a number of pulse signals as detection signals to a data processing unit 4, the number corresponding to the number of the received ions.

The data processing unit 4 includes a storage unit 41, and further includes a non-selection ion setting unit 42, a product ion scan execution unit 43, a product ion selection unit 44, and an MRM transition determination unit 45 as its functional blocks. Moreover, the data processing unit 4 is configured to exchange signals as appropriate with a controlling unit 5 for controlling the operations of units such as: the pump 11 and the injector 12 of the liquid chromatograph unit 1; and the power supply unit 24 and a CID gas supply unit (not illustrated) of the mass spectrometer 2. The actual body of the data processing unit 4 is a personal computer, and functions as the data processing unit 4 can be fulfilled by executing data processing software installed in advance in the computer. Moreover, an input unit 6 and a display unit 7 are connected to the data processing unit 4.

Figure 2:
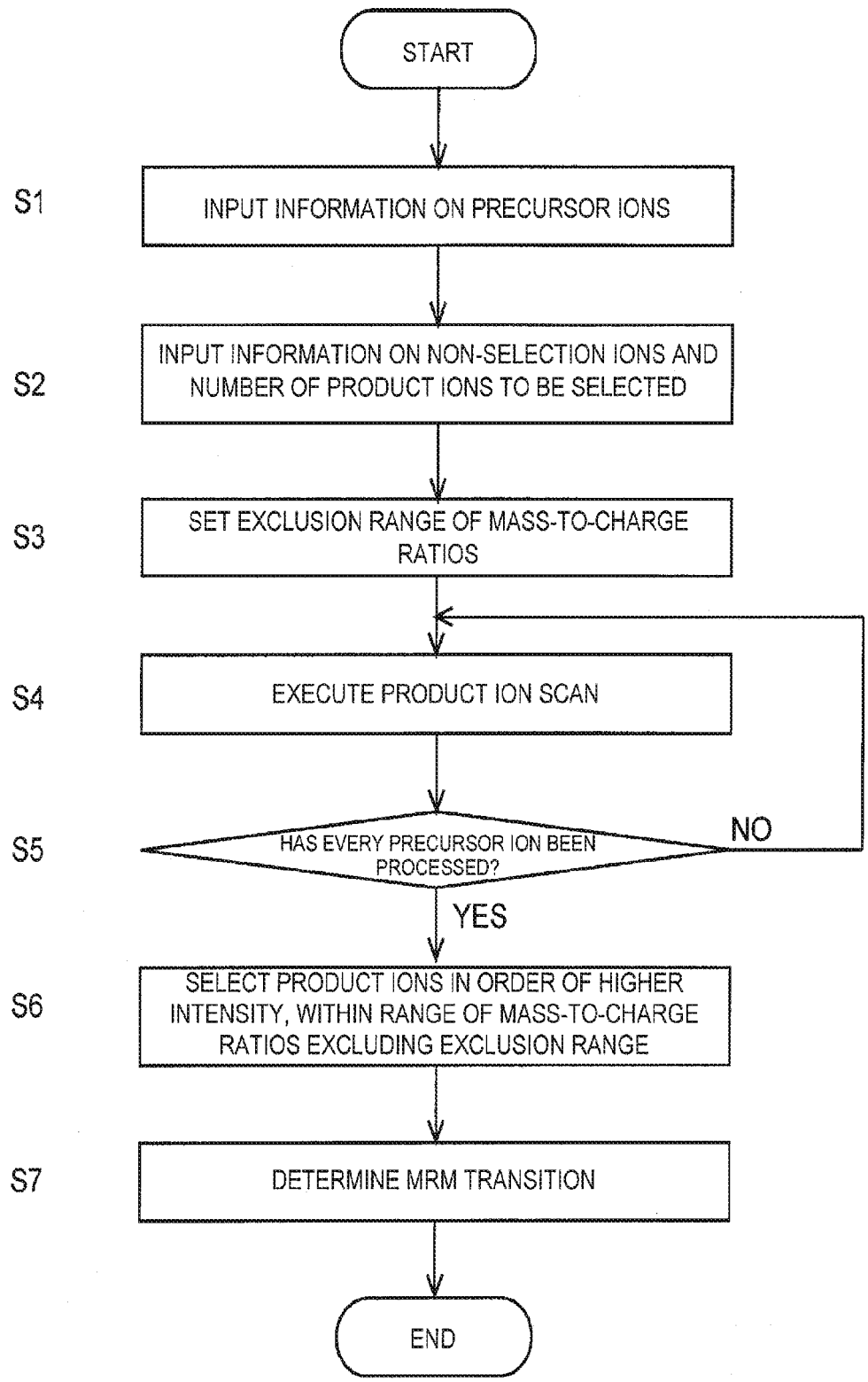
FIG. 2 is a flowchart for describing an embodiment of a mass spectrometric method according to the present invention.
Figure 3:
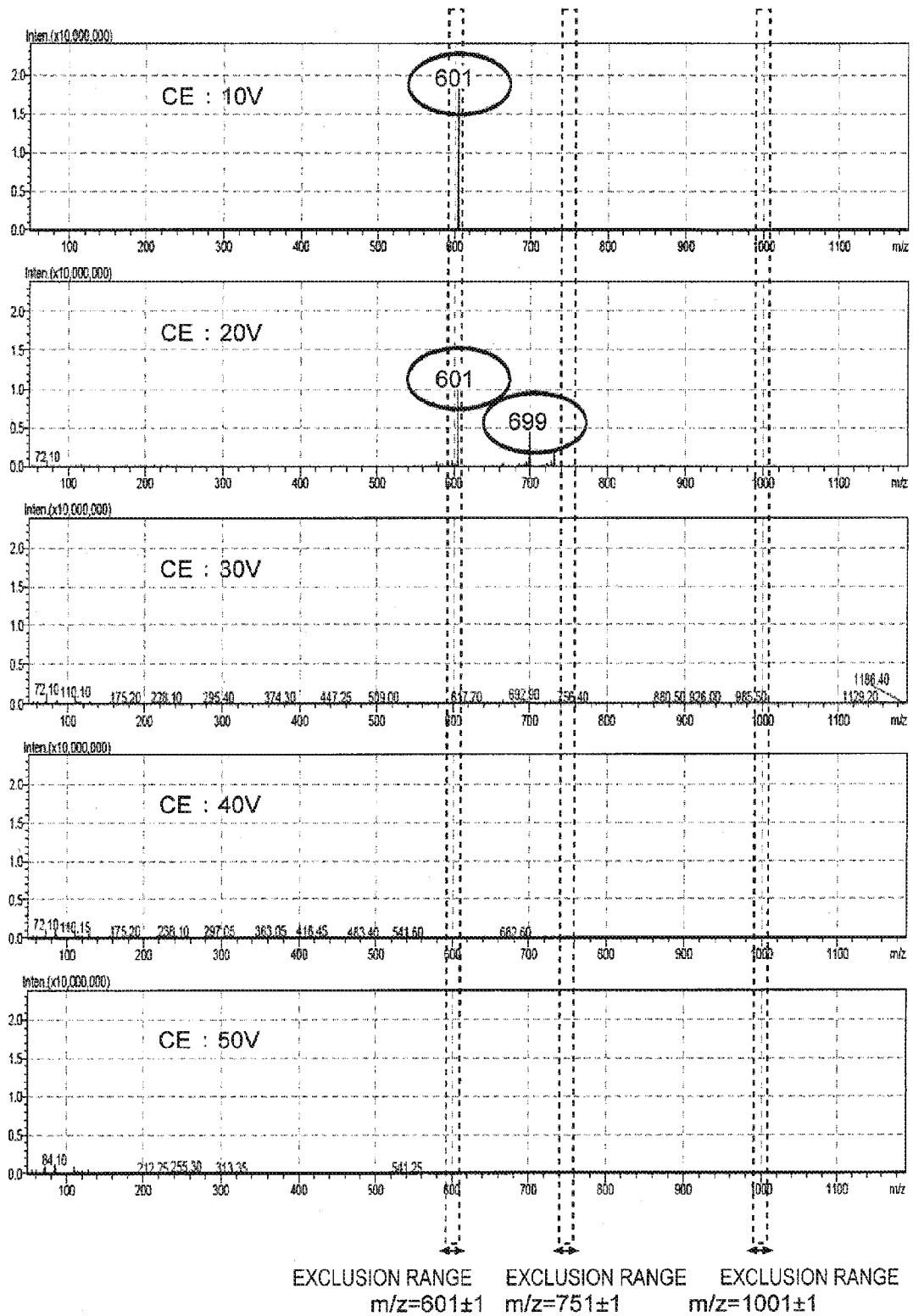
FIG. 3 illustrates a product ion spectrum obtained according to a mass spectrometric method of the present embodiment.

Hereinafter, a method of determining MRM measurement conditions using the liquid chromatograph mass spectrometer of the present embodiment is described. FIG. 2 is a flowchart of processing performed at the time of determining the MRM measurement conditions, and FIG. 3 illustrates a product ion spectrum example obtained by performing product ion scan using the liquid chromatograph mass spectrometer of the present embodiment.

First, an analysis operator defines, as a precursor ion, one or more ions that appear as a peak having intensity equal to or more than a predetermined value on a mass spectrum obtained by performing MS analysis in advance on a target compound, and inputs information on the mass-to-charge ratios of the precursor ions and the like from the input unit 6 (Step S1). The analysis operator further inputs, for each precursor ion, information on non-selection ion and the number of product ions to be selected (Step S2). Although the information on non-selection ion is typically a numerical value of the mass-to-charge ratio, an ionic formula may be input as the information instead. In the present embodiment, one kind of pentavalent ion having a mass-to-charge ratio m/z=601 is selected as the precursor ion, and the value of the mass-to-charge ratio (m/z=601) and the valence (pentavalence) are input as the information on the non-selection ion. That is, the selected precursor ion is set as the non-selection ion. This is to avoid a trouble that, in the case where the precursor ion is not fragmented in the collision cell but detected as it is, such ion is set to an MRM transition. Moreover, the number of product ions to be selected is set to one.

The number of kinds of precursor ions and the number of product ions to be selected can be changed as appropriate. Moreover, in addition to the above-mentioned example, ions from which information that characterizes the target compound cannot be obtained (for example, isotope ions of the precursor ion, ions in which the mass does not change and only the valence of the precursor ion changes, and dehydrated ions of the precursor ion) can be set as appropriate as the non-selection ion.

After the analysis operator inputs the precursor ion, the information on non-selection ion concerning the precursor ion, and the number of product ions to be selected, the non-selection ion setting unit 42 sets a mass-to-charge ratio corresponding to the non-selection ion. For example, in the case where the analysis operator inputs a value of the mass-to-charge ratio, the non-selection ion setting unit 42 sets the range of ±1 u about the value (that is, the range of mass-to-charge ratios in which ions can be regarded as identical ion) to an exclusion range. In the case where the analysis operator inputs a molecular formula concerning the non-selection ion, the non-selection ion setting unit 42 obtains a value of the mass-to-charge ratio from the molecular formula, and sets a range having a predetermined width (for example, ±1 u) about the value to the exclusion range of mass-to-charge ratios (Step S3). In the present embodiment, an exclusion range of m/z=600 to 602 is set with regard to the mass-to-charge ratio m/z=601 of the non-selection ion.

Moreover, based on the value of the mass-to-charge ratio and the valence input by the analysis operator, the non-selection ion setting unit 42 assumes that the precursor ion is $(M+5H)^{5+}$, and calculates mass-to-charge ratios of ions in which the precursor ion is not fragmented but only the valence changes to each of monovalence to tetravalence. That is, the non-selection ion setting unit 42 calculates the mass-to-charge ratios respectively corresponding to $(M+H)^+$, $(M+2H)^{2+}$, $(M+3H)^{3+}$, and $(M+4H)^{4+}$, as m/z=3001, 1501, 1001, and 751. Then, the non-selection ion setting unit 42 automatically adds and sets ranges (m/z=750 to 752 and 1000 to 1002) respectively having predetermined widths about values (m/z=751 and 1001) within the range of mass-to-charge ratios (in the present embodiment, m/z=50 to 1200) to be subjected to product ion scan measurement, as the exclusion ranges of mass-to-charge ratios.

After the exclusion ranges of mass-to-charge ratios are set, the product ion scan execution unit 43 outputs a predetermined signal to the controlling unit 5, and executes product ion scan on a first precursor ion within the preset range of mass-to-charge ratios (m/z=50 to 1200). During the elution period of the sample solution, the product ion scan is executed under a plurality of conditions that the magnitude of the collision energy applied to the collision cell is different, and a product ion spectrum is acquired for each product ion scan event by time-averaging the detected intensity of ions obtained under each condition (Step S4). Moreover, the product ion scan execution unit 43 stores the acquired product ion spectra in the storage unit 41, and displays them on a screen of the display unit 7. In the present embodiment, the product ion scan is repetitively executed under five conditions that the magnitude of the collision energy (CE) is different (CE: 10 V, 20 V, 30 V, 40 V, and 50 V), and a product ion spectrum is acquired for each product ion scan event (see FIG. 3). From the product ion spectra in FIG. 3, it is understood that: a strong peak (m/z=601) of the precursor ion appears under the condition that the CE is as small as 10 V and 20 V; and the precursor ion is not fragmented in the collision cell 232 but detected as it is.

After the product ion scan is ended, the product ion scan execution unit 43 determines whether or not the product ion scan has been completed for every precursor ion input by the analysis operator (Step S5). Although the number of kinds of precursor ions is defined as one in the present embodiment, in the case where a plurality of precursor ions is set, the product ion scan is executed while the precursor ions are sequentially changed, and a product ion spectrum is acquired for every precursor ion.

When the product ion scan has been completed for every precursor ion (YES in Step S5), the product ion selection unit 44 selects mass peaks equal to the number of selected product ions specified by the analysis operator and execution conditions (such as collision energy) for the product ion scan by which the selected peaks are obtained, in the order of higher intensity on every product ion spectrum (Step S6). At this time, mass peaks existing in the exclusion ranges set by the non-selection ion setting unit 42 are excluded. In the example of FIG. 3, mass peaks at m/z=601 on the mass spectra obtained when the CE is 10 V and 20 V are peaks within the exclusion range, and hence ions corresponding to these peaks are not selected.

Lastly, the MRM transition determination unit 45 determines a pair of a precursor ion and a product ion corresponding to the selected mass peak, as an MRM transition (Step S7). Moreover, the MRM transition determination unit 45 creates a method file in which the MRM transition is associated with the execution conditions for the product ion scan.

In the present embodiment, as a result of executing the above-mentioned steps, a pair of a precursor ion having m/z=601 and a product ion having m/z=699 is determined as an MRM transition, and an MRM method in which the CE is 20 V as an execution condition for MRM measurement is created. In the present embodiment, the reason why the mass-to-charge ratio of the product ion is larger than the mass-to-charge ratio of the precursor ion is that the valence of ion decreases in the collision cell.

In the case where the product ion spectra as illustrated in FIG. 3 are obtained, because a mass peak having the highest intensity is automatically selected according to a conventional method, the peak having m/z=601 on the product ion spectrum acquired under the condition that the CE is 10 V is selected. However, as described above, this peak is a mass peak corresponding to the precursor ion itself, and is inappropriate as a product ion because the product ion cannot characterize a target compound.

Similarly, as described above, isotope ions of the precursor ion, ions in which only the valence of the precursor ion changes, dehydrated ions of the precursor ion, and the like are inappropriate as a product ion. However, in the case where the intensity of a mass peak corresponding to such ions is high, such ions are selected.

Meanwhile, using the mass spectrometer and the mass spectrometric method of the present embodiment, even if the intensity of a mass peak on a product ion spectrum is high, undesired product ions are not selected. Accordingly, a product ion suited for measurement on a target compound can be selected, and an MRM transition having a pair of the selected product ion and the precursor ion corresponding to the selected product ion can be determined.

The above-mentioned embodiment is merely an example, and can be changed as appropriate along the gist of the present invention.

In the above-mentioned embodiment, the case of the liquid chromatograph mass spectrometer is taken, but the apparatus configuration is not limited to this case. Any apparatus configuration may be adopted as long as a mass spectrometer is used.

Moreover, in the above-mentioned embodiment, the mass-to-charge ratios of ions having different valences are also set as exclusion ranges with respect to one multivalent ion input as a non-selection ion by the analysis operator. In addition, exclusion ranges of a plurality of mass-to-charge ratios other than the above-mentioned mass-to-charge ratios can be set based on information on precursor ions and information on non-selection ions input by the analysis operator. For example, in the case where the analysis operator inputs a molecular formula of a precursor ion, isotope ions, dehydrated ions, and the like of the precursor ion may be automatically set as a non-selection ion.

Further, in the above-mentioned embodiment, description is given of the example case where the product ion scan is executed under the plurality of conditions that only the magnitude of the collision energy (CE) is different. Alternatively, for example, the product ion scan may be executed under conditions that the resolutions of Q1 and Q3 and the like are different as appropriate, and an MRM transition may be determined from product ion spectra thus obtained.

REFERENCE SIGNS LIST

1 . . . Liquid Chromatograph Unit
  10 . . . Mobile-Phase Container
  11 . . . Pump
  12 . . . Injector
  13 . . . Column
2 . . . Mass Spectrometer
  20 . . . Ionization Chamber
    201 . . . Electrospray Ionization Probe
    202 . . . Heating Capillary
  21 . . . First Intermediate Vacuum Chamber
    211 . . . Ion Guide
    212 . . . Skimmer
  22 . . . Second Intermediate Vacuum Chamber
    221 . . . Ion Guide
  23 . . . Analysis Chamber
    231 . . . Front-Stage Quadrupole Mass Filter
    232 . . . Collision Cell
    233 . . . Multipole Ion Guide
    234 . . . Rear-Stage Quadrupole Mass Filter
    235 . . . Ion Detector
  24 . . . Power Supply Unit
4 . . . Data Processing Unit
  41 . . . Storage Unit
  42 . . . Non-Selection Ion Setting Unit
  43 . . . Product Ion Scan Execution Unit
  44 . . . Product ion Selection Unit
  45 . . . MRM Transition Determination Unit
5 . . . Controlling Unit
6 . . . Input Unit
7 . . . Display Unit

The invention claimed is:

1. A mass spectrometric method, using a mass spectrometer having a mass separation unit before and after a collision cell for fragmenting ions, for selecting a product ion corresponding to a precursor ion set for a sample by performing product ion scan with respect to the precursor ion, the method comprising:
  a) setting one or a plurality of mass-to-charge ratios based on information on non-selection ions input by a user; and
  b) selecting a product ion that satisfies a predefined criterion within a range excluding the one or plurality of mass-to-charge ratios in a product ion spectrum obtained by the product ion scan.

2. The mass spectrometric method according to claim 1, wherein the one or plurality of mass-to-charge ratios are set as a range having a width.

3. The mass spectrometric method according to claim 2, wherein the width is determined in accordance with a command input by the user.

4. The mass spectrometric method according to claim 3, wherein a number of product ions are selected, the number being indicated by the command input by the user.

5. The mass spectrometric method according to claim 2, wherein a number of product ions are selected, the number being indicated by the command input by the user.

6. The mass spectrometric method according to claim 1, wherein a number of product ions are selected, the number being indicated by the command input by the user.

7. A mass spectrometer having a mass separation unit before and after a collision cell for fragmenting ions, the mass spectrometer being for selecting a product ion corresponding to a precursor ion set for a sample by performing product ion scan with respect to the precursor ion, the mass spectrometer comprising:
  a) a non-selection ion setting unit for setting one or a plurality of mass-to-charge ratios based on information on non-selection ions input by a user; and
  b) a product ion selection unit for selecting a product ion that satisfies a predefined criterion within a range excluding the set one or plurality of mass-to-charge ratios in a product ion spectrum obtained by the product ion scan.

8. A non-transitory compute computer readable media recording a mass spectrometric data processing program, using a mass spectrometer having a mass separation unit before and after a collision cell for fragmenting ions, for selecting a product ion corresponding to a precursor ion from a product ion spectrum obtained set for a sample by performing product ion scan with respect to the precursor ion, the mass spectrometric data processing program causing a computer capable of accessing a storage unit in which the product ion spectrum is stored to function as:
- a) a non-selection ion setting unit for setting one or a plurality of mass-to-charge ratios based on information on non-selection ions input by a user; and
- b) a product ion selection unit for selecting a product ion that satisfies a predefined criterion within a range excluding the one or plurality of mass-to-charge ratios in a product ion spectrum obtained by the product ion scan.

* * * * *